US006452034B2

(12) United States Patent
Cruse

(10) Patent No.: US 6,452,034 B2
(45) **Date of Patent: *Sep. 17, 2002**

(54) LOW-SULFUR POLYSULFIDE SILANES AND PROCESS FOR PREPARATION

(75) Inventor: Richard W. Cruse, Yorktown Heights, NY (US)

(73) Assignee: Crompton Corporation, Middlebury, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/477,394

(22) Filed: Jan. 4, 2000

(51) Int. Cl.[7] .................................................. C07F 7/08

(52) U.S. Cl. ...................................................... 556/427

(58) Field of Search ......................................... 556/427

(56) References Cited

U.S. PATENT DOCUMENTS

| | | | | |
|---|---|---|---|---|
| 3,451,458 A | | 6/1969 | Stueber | 152/330 |
| 3,842,111 A | | 10/1974 | Meyer-Simon et al. | 260/448.2 |
| 3,873,489 A | | 3/1975 | Thurn et al. | 260/33.6 |
| 3,946,059 A | | 3/1976 | Janssen et al. | 260/448.2 |
| 3,978,103 A | | 8/1976 | Meyer-Simon et al. | 260/448.8 |
| 3,997,581 A | | 12/1976 | Pletka et al. | 260/448.8 |
| 4,072,701 A | | 2/1978 | Pletka et al. | 260/448.8 |
| 4,129,585 A | | 12/1978 | Buder et al. | 260/448.8 |
| 4,384,132 A | | 5/1983 | Schwarz et al. | 556/427 |
| 4,408,064 A | | 10/1983 | Schwarz et al. | 556/427 |
| 4,444,936 A | | 4/1984 | Schwarz et al. | 524/393 |
| 4,507,490 A | | 3/1985 | Panster et al. | 556/427 |
| 4,704,414 A | | 11/1987 | Kerner et al. | 523/213 |
| 5,110,969 A | | 3/1992 | Dittrich et al. | 556/427 |
| 5,227,425 A | | 7/1993 | Rauline | 524/493 |
| 5,405,985 A | | 4/1995 | Parker et al. | 556/427 |
| 5,468,893 A | | 11/1995 | Parker et al. | 556/427 |
| 5,663,395 A | * | 9/1997 | Gobel et al. | 556/427 |
| 5,674,932 A | | 10/1997 | Agostini et al. | 524/430 |
| 5,753,732 A | | 5/1998 | Wideman et al. | 524/263 |
| 5,965,760 A | * | 10/1999 | Michel et al. | 556/427 |
| 6,140,524 A | * | 10/2000 | Ichinohe et al. | 556/427 |

FOREIGN PATENT DOCUMENTS

| | | |
|---|---|---|
| DE | 2405758 | 8/1975 |
| DE | 197 02 046 | 1/1998 |
| EP | 0 217 178 A2 | 4/1987 |
| EP | 0 773 224 A2 | 5/1997 |
| EP | 0 845 472 | 6/1998 |
| EP | 0 732 362 B1 | 6/1999 |
| JP | 57 005724 | 1/1982 |
| WO | 9909036 | 2/1999 |

OTHER PUBLICATIONS esp@net abstract for DE 19702046 (abstracting EP 0819694), 1999.

esp@net abstract for EP 0773224 (abstracting US 5663395), 1999.

Harpp et al., "Organic Sulfur Chemistry. 42. Sulfur–Sulfur Bond Cleavage Processes. Selective desulfurization of Trisulfides"; J. Am. Chem. Soc. (1982), 104(22), 6045–6053.

Wojnowski et al., "Beitraege Zur Chemie Der Silicium–Schwefel–Verbindungen. 50 1 Bis(Triorganoxysilyl)Polysulfide Und Die Struktur Des Bis(Tri–T–Butoxysilyl)Disulfids" Zeitschrift Fur Anorganische Und Allgemeine Chemie; vol. 561, (1988) pp. 167–173.

* cited by examiner

*Primary Examiner*—Paul F. Shaver
(74) *Attorney, Agent, or Firm*—Michael P. Dilworth

(57) ABSTRACT

An improvement on existing methods to desulfurize oligosulfide silanes generates no added raw materials or waste streams in addition to the sodium chloride which is generated as a byproduct in the current manufacturing process for polyusulfide silanes. This is accomplished by using mercaptosilane salts as desulfurizing agents, which yield more product in addition to that already obtained from the desulfurized silane of higher sulfur rank. The process simply entails reacting an oligosulfide silane with a mercaptosilane salt to thereby obtain an oligosulfide silane whose average sulfur rank is less than the starting oligosulfide silane. Coproduct sulfide salts can be recycled back to the oligosulfide manufacturing process. The mercaptosilane salts are novel materials as well.

20 Claims, No Drawings

LOW-SULFUR POLYSULFIDE SILANES AND PROCESS FOR PREPARATION

BACKGROUND OF THE INVENTION

The invention relates to a method of preparing polysulfide-functional silanes composed of novel sulfur rank distributions, i.e., distributions which do not form from the practiced prior art.

Sulfur-containing silane coupling agents are particularly useful in providing rubber tires, including automotive tires, with improved properties, generally by coupling inorganic fillers or fibers with the rubber matrix in a fashion which leads to the improved properties. The sulfur-containing silane coupling agents which have achieved commercial success to date have been produced by disadvantageous processes which involve large quantities of chlorine-containing by-products.

A number of variations have been proposed for the preparation of oligosulfide-functional silanes starting from the chloroalkyl silane starting materials and involving sulfur and/or a sulfur anion. This art is described in the following U.S. Patents: U.S. Pat. No. 3,842,111; U.S. Pat. No. 3,873,489; U.S. Pat. No. 3,946,059; U.S. Pat. No. 3,978,103; U.S. Pat. No. 3,997,581; U.S. Pat. Nos. 4,072,701; 4,129,585; U.S. Pat. No. and 4,507,490; U.S. Pat. No. 5,405,985 and U.S. Pat. No. 5,468,893. This art is limited to the use of an integral mole ratio of sulfur reacted to bis-silylalkyl oligosulfide product obtained. The art teaches that in this preparation, only a single oligosulfide species is obtained, in which the number of sulfur atoms present in each molecule is dependent on the ratio of sulfur to starting chloroalkyl silane used in the preparation. The art does not teach the generation of distributions of species of different molecular sulfur content. The art suggests that the exclusive formation of a specific oligomer can be controlled by controlling the amount of sulfur used in the preparation. Elemental analyses and NMR data are provided in the examples to support these conclusions.

Other art describes another method which yielded similar substances, but starting from alkenyl silane starting materials instead of the aforementioned chloroalkyl silane starting materials. This art is described in the following U.S. Patents: U.S. Pat. No. 4,384,132; U.S. Pat. No. 4,408,064; and U.S. Pat. No. 4,444,936. This art implies the formation of distributions of the corresponding oligosulfide silane derivatives.

More recently, art has been described which fully recognizes and embraces the notion that distributions of oligosulfide silanes of different individual molecular sulfur content are obtained in efforts to prepare any of the oligosulfide silanes, and that it is useful to regard this mixture from the standpoint of the average molecular sulfur content. This art was described in EP 0 773 224 A2 and in U.S. Pat. No. 5,674,932. It is clear from these disclosures that the total sulfur content of the oligosulfide silane mixtures can be controlled within a wide range by adjusting the amount of sulfur introduced into their preparation. What is difficult to control, however, is the way in which this sulfur becomes distributed among the individual oligosulfide silanes, hereafter referred to as "sulfur ranks", in which this term is taken to mean the number of sulfur atoms linked by sulfur-sulfur bonds in a molecule of the oligosulfide silane. Any given ratio of total sulfur to silicon introduced into the preparation tends to yield a single or only narrowly variant specific sulfur rank distribution which is dependent only on the aforementioned ratios of reactants used and which is essentially independent of the way in which the reaction is carried out. Thus, no good method is described in the prior art which allows one to control the way the sulfur distributes itself among the individual oligosulfides. The total amount of sulfur can be controlled, but the system controls the way this sulfur is distributed.

The aforementioned inability to control the distribution of sulfur has a special commercial significance in the manufacture of disulfide-functional silanes for applications as coupling agents in filled elastomers. Recent disclosures in, DE 197 02 046 A1, U.S. Pat. No. 5,674,932 and EP 0 732 362 A1, teach that disulfide-functionalized silanes offer advantages over higher sulfur ranks for use in mineral-filled elastomer compositions. However, preparation of disulfide silane compositions by the methods known from the aforementioned prior art, in which the average sulfur rank is two, yields a substantial portion of the thioether silane. This is a disadvantage because this particular species has a sulfur rank of one, and is widely considered to be an inactive diluent. A second disadvantage is that to average a sulfur rank of two, some of the individual oligosulfide silane species must have a sulfur rank greater than two, which further detracts from the advantages reaped by use of the disulfide silane.

The preparation of pure or nearly pure disulfide compositions cannot be carried out by the processes described above. Even compositions which are not necessarily pure, but different from preparations which arise naturally by the aforementioned synthetic pathways, cannot be prepared either by those processes. The preparation of any such compositions would require more elaborate and more economically disadvantaged methods. Only examples of such methods limited specifically to the preparation of essentially pure disulfide silanes, are described in the prior art. Thus, the use of sulfuryl chloride or iodine to oxidize mercaptosilanes to the corresponding disulfide, is taught in DE-PS 2 360470 and EP 0 217 178 A1, respectively. These methods are disadvantaged. The mercaptosilane would have to be prepared by a method very similar to the aforementioned prior art for the preparation of oligosulfide silanes in a first step. A separate second step would then be needed, which requires the use of corrosive and/or expensive materials to convert the mercaptan to the disulfide, and which furthermore produces undesirable waste products. Thus, not only is a process required involving two separate steps, but there is also a necessity to deal with additional reagents, waste streams, and special hazards and inconveniences associated with the use of these materials. Other methods would include oxidizers based on oxygen, such as manganese dioxide, chromates, dichromates, or molecular oxygen optionally with an appropriate catalyst, but their use is precluded because water would be coproduced with their use.

A second type of a two-step method, again limited to the preparation of pure or nearly pure disulfide compositions, has recently been taught in EP 0 773 224 A2, in which an oligosulfide silane or oligosulfide silane mixtures containing components with a chain of more than two sulfur atoms is desulfurized to yield a product, all of whose components contain chains of a maximum of two sulfur atoms. In its simplest form, this document describes the desulfurization of a mixture of oligosulfide silanes to yield essentially pure disulfide, free of higher sulfur ranks. In its most general form, this amounts to the desulfurization of a mixture of oligosulfide silanes to yield a product mixture of oligosulfide silanes consisting only of the disulfide and thioether.

The procedures described in EP 0 773 224 A2 require desulfurization reagents such as cyanides, sulfites, and trivalent phosphorus compounds to remove sulfur from the oligosulfide silane to yield thiocyanates, thiosulfates, and the corresponding thionophosphorus derivatives, respectively. Although each of these types of reagents very effectively removes the excess sulfur, the use of each of them also presents some problems. Cyanides can be toxic. Sulfites do not dissolve readily in the preferred alcohol solvents, nor in any other readily used organic solvents, necessitating the use of water and with it, the need to take measures to prevent decomposing the hydrolyzable groups on silicon. Trivalent phosphorus compounds are expensive and can contaminate the final product. In addition to these shortcomings, only a single mole of sulfur is removed per mole of desulfurizing agent used. The molecular weight of these desulfurization agents can easily be several times that of a sulfur atom.

Furthermore, the method of EP 0 773 224 A2 is described, in particular, for the use with a tetrasulfide starting material, requiring the removal of two sulfur atoms. Thus, the overall indirect preparation of disulfides by first preparing tetrasulfides, and then treating with large amounts of desulfurizing agents, adds a considerable raw material requirement and waste stream to the overall process of making disulfide silanes. As in the two-step process starting from mercaptosilanes described in DE-PS 2 360470 and EP 0 217 178 A1, the preparation of disulfide silane compositions by this method requires, in addition to requiring a total of two steps, also the necessity to deal with additional reagents, waste streams, and hazards associated with the use of these materials.

There remains a need for a process that can simply and efficiently prepare polysulfide-functional silanes composed of novel sulfur rank distributions, i.e., distributions which do not form from the practiced prior art. In particular, there is a need for such a process that can assure high activity of sulfur-containing silane coupling agents for use in filled rubber compositions, especially for use in the production of low rolling resistance tires.

BRIEF DESCRIPTION OF THE INVENTION

A method is described in which an oligosulfide silane containing a chain of more than two sulfur atoms, or a mixture thereof is partially or completely desulfurized to form a new oligosulfide silane or mixture thereof whose average sulfur rank is less than the starting silane or mixture thereof. In one aspect, the invention provides a method for removing polysulfidic sulfur from an oligosulfide silane containing a chain of more than two sulfur atoms, or a mixture thereof, comprising: reacting an oligosulfide silane with a mercaptosilane salt to obtain an oligosulfide silane or mixture thereof whose average sulfur rank is less than the starting oligosulfide silane or mixture thereof. Another aspect of the invention is the mercaptosilane salt used to conduct such desulfurization.

In this method, sulfur is removed in such a way that only polysulfidic sulfur is removed from the oligosulfide silanes. As used herein, the term, polysulfidic sulfur is taken to mean sulfur atoms chemically bonded only to other sulfur atoms. Thus, the method of the present invention can remove sulfur from oligosulfide silane components of sulfur rank 3 or higher to yield oligosulfide silane components containing less sulfur than the starting components, but retaining a minimum of two sulfur atoms. Disulfide silane components are not further desulfurized. Thioether silane components (monosulfides) remain inert to the desulfurization process. No extraneous chemical groups or atoms, such as cyanide, phosphorus, sulfite, thiosulfate, or thiocyanate are introduced or formed to require steps for removal, to become a disposal issue, or to remain as impurities in the product.

DETAILED DESCRIPTION OF THE INVENTION

It is an object of the invention to prepare polysulfide-functional silanes composed of sulfur rank distributions. Another aspect of the invention are novel salts of mercaptosilanes. The polysulfide-functional silanes of the present invention are novel in that they contain less of the thioether, and more of the disulfide and/or higher sulfur ranks than do the compositions prepared from the same oligosulfide anion distribution by the prior art.

The present invention describes the preparation of oligosulfide silane compositions by a novel chemical method for desulfurization of different oligosulfide silane compositions. The term "oligosulfide silane" shall refer to any single component or mixture of components, the structure of whose individual chemical components may be represented by Formula 1:

$$X^1X^2X^3SiG\text{-}S_n\text{-}GSiX^1X^2X^3 \quad \text{Formula (1)}$$

In Formula (1), each occurrence of G is independently a divalent alkyl, alkenyl, aryl or aralkyl group which has from 1 to 18 carbon; each occurrence of $X^1$, $X^2$, and $X^3$ is independently a group selected from the group consisting of RO— and R—, wherein each R is independently alkyl, alkenyl, aryl or aralkyl wherein R can contain from 1 to 18 carbon; and at least one of $X^1$, $X^2$, and $X^3$ is RO—. Also in Formula (1), each n is an integer from 2 to 20, preferably 2 to 8, and most preferably 2 to 4. In the oligosulfide silanes to be treated, n=3 to 8 (and in the course of the process n would be reduced such that n=2 to 8). It is recognized that mixtures of oligosulfide silanes will contain species where n=1 or 2; however these are not the components on which treatment will have an effect.

As used herein, "alkyl" includes straight, branched and cyclic alkyl groups, and "alkenyl" includes straight, branched and cyclic alkenyl groups containing one or more carbon-carbon double bonds. Specific alkyls include methyl, ethyl, propyl, isobutyl, and specific aralkyls include phenyl, tolyl and phenethyl. As used herein, "cyclic alkyl" or "cyclic alkenyl" also includes bicyclic and higher cyclic structures, as well as cyclic structures further substituted with alkyl groups. Representive examples include norbornyl, norbornenyl, ethylnorbornyl, ethylnorbornenyl, ethylcyclohexyl, ethylcyclohexenyl, and cyclohexylcyclohexyl.

Representative examples of starting oligosulfide silanes include bis-(3-triethoxysilyl-1-propyl)trisulfide, bis-(3-triethoxysilyl-1-propyl)tetrasulfide (TESPT), bis-(diethoxymethylsilylmethyl)trisulfide, bis-(triethoxysilylmethyl)trisulfide, bis-(triethoxysilylmethyl) tetrasulfide, bis-(2-diethoxymethoxysilyl-1-ethyl)trisulfide, bis-(2-triethoxysilyl-1-ethyl)trisulfide, bis-(2-triethoxysilyl-1-ethyl)tetrasulfide, bis-(1-triethoxysilyl-1-ethyl) tetrasulfide, bis-(3-methoxydimethylsilyl-1-propyl) tetrasulfide, and bis-(3-triisopropoxysilyl-1-propyl) trisulfide.

The preferred embodiments of the present invention include oligosulfide silane compositions represented by Formula (1) in which: $X^1$, $X^2$, and $X^3$ are ethoxy, methoxy, or alkyl, where ethoxy, methoxy, and methyl are particularly preferred, and ethoxy is most preferred; and in which G is $—CH_2—$, $—CH_2CH_2—$, $—CH_2CH_2CH_2—$, or $—CH_2(CH_2)_mCH_2—$ where m is an integer between 2 and 16, and where $—CH_2—$, $—CH_2CH_2—$, and $—CH_2CH_2CH_2—$ are particularly preferred, and $—CH_2CH_2CH_2—$ is most preferred. The most preferred oligosulfide silane compositions represented by Formula (1) are bis-(3-triethoxysilyl-1-propyl) oligosulfides with varying n.

An oligosulfide silane composition suitable for desulfurization can be obtained from any suitable source, such as preparation by one of the methods known in the art, such as described in the literature cited above. The resulting composition typically comprises a distribution of sulfur ranks whose total sulfur content can be controlled by the amount of sulfur used in its preparation, but whose distribution is not controllable.

To desulfurize an oligosulfide silane, a salt of a mercaptosilane (Formula 2) is used. The term salt is used to refer to an anion cation pair wherein the anion is the mercaptosilane. Such salts may be represented by the formula (2) $X^1X^2X^3SiG^1\text{-}S^-Z^+$ wherein $X^1$, $X^2$, $X^3$, and $G^1$ have the same meaning as previously described (with $G^1$ being the same as G) and $Z^+$ is a Group 1–3 metal cation, an alkyl ammonium or ammonium ($NH_4^+$). If $G^1$ is different than G, then mixed, non-symmetrical, sulfur silanes may be formed.

The mercaptosilane starting material (i.e., $X^1X^2X^3SiG^1\text{-}SH$) for the salt is prepared by methods known in the art or is commercially available, e.g. SILQUEST A-1891 silane from CK Witco Corp. This mercaptosilane is deprotonated, or deprotonated in situ during desulfurization of the polysulfide silane to the corresponding mercaptide salt. Preferably, this is done with a pure mercaptosilane (i..e., there are no other sulfur containing silanes present in the process, especially polysulfide silanes) to yield the pure salt. The salts may be placed in solvents that are used for the desulfurization process or the deprotonation process may be conducted in such solvents Suitable bases to form the salt of the mercaptosilane must be strong enough to deprotonate the mercaptan, without containing or generating water, which bases include alkoxides, hydrides, amides, and organo-alkali metal compounds. Metallic alkali metals also could be used to deprotonate the mercaptosilane, and would release hydrogen gas in the process. The preferred bases are sodium or potassium alkoxide or metallic sodium. The alkali metal alkoxide of the alcohol corresponding to the silane alkoxy group would be preferred if a single kind of alkoxy group is desired in the silane product. Preferred counterions (cations) ($Z^+$) are those whose sulfides and polysulfides are slightly soluble (preferably <0.1 weight percent), most preferably totally insoluble, and whose mercaptides are readily soluble in the chosen solvent. Sodium is most preferred on the basis of the availability of starting materials The oligosulfide silane composition is desulfurized by reaction with the mercaptosilane salt. In this reaction, one or more polysulfidic sulfur atoms (polysulfidic sulfur is sulfur chemically bound only to sulfur) from a molecule of the oligosulfide silane composition of sulfur rank three or greater is removed. This reaction generates a silane of correspondingly lower sulfur rank. The two mercaptide anions are concomitantly coupled to yield a molecule of disulfide silane. Again, if G and $G^1$ are different from each other, non-symmetrical silanes may result. Thus, the reaction of the invention produces oligosulfide silanes from both the original oligosulfide silane of higher sulfur rank as well as from the mercaptosilane. The only other product obtained is a sulfide and/or polysulfide salt (e.g., sodium sulfide), which can be recycled into the preparation of the reactants. No waste products are produced from this process (wherein p=1 to 16) (Reaction 1).

$$2X^1X^2X^3SiG\text{–}S^- + X^1X^2X^3SiG\text{-}S_n\text{-}GSiX^1X^2X^3 \rightarrow X^1X^2X^3SiG\text{-}S_2\text{-}GSiX^1X^2X^3 + X^1X^2X^3SiG\text{-}S_{n-p}GSiX^1X^2X^{3-} + S_p^- \qquad \text{Reaction 1}$$

The reaction preferably is run in a solvent, though it is not necessary if the reaction is run under conditions under which the sulfur silanes are liquid. Alcohols are the preferred solvents because they readily dissolve the mercaptides, mediate the chemical reactions readily, and lead to coarse precipitates which are readily filtered. Other solvents, however, can be used as well, such as ethers, tetrahydrofuran, polyethers, glyme, diglyme and higher glymes, aromatic solvents such as toluene and xylene if the mercaptide is sufficiently soluble, dimethylformamide, and dimethylsulfoxide. If an alcohol is used, it is preferable that it matches the alkoxides of the silanes so that transesterification does not occur (unless such transesterification is desired). An example would be the use of methoxy oligosulfide silane compositions, with the ethoxy or methoxy mercaptosilane in ethanol, removing the solvent by fractional distillation and generating a mixed alkoxy silane.

The reaction temperature is not critical, but may be run at ambient temperature to reflux of the solvent, preferably 0 to 100° C. and most preferably ambient to 78° C. The pressure under which the reaction is run is not critical. The reaction may be run under vacuum to strip ethanol or any volatile gases, or may be run under pressure to keep such gases in the reactor.

The products prepared according to the present invention can be used in any system wherein mercaptosilanes are known for use, i.e., as coupling agents between organic and inorganic systems or as crosslinkers. Mercaptosilanes are particularly useful in free radical cured systems. They also may be used in adhesives for metals such as lead, copper, and silver. Another use would be as coupling agents in mineral-filled polyphenylene sulfide.

The products prepared according to the invention most suitably are employed in natural and synthetic rubber compositions and blends, in amounts consistent with those previously employed for other silane coupling agents for the use in sulfur-vulcanizable, silica-reinforced tire rubber compositions. Exemplary of suitable amounts will be at least 2 parts per hundred parts rubber (PHR) and, preferably from about 4 to about 20 PHR, e.g., 6 to 12 PHR. The amount will also be related to the amount of silica employed, preferably the ratio by weight of silica to silane being in the range of from 4:1 to about 40:1, more narrowly from about 6:1 to about 10:1. Molar ratios of added sulfur for vulcanization to sulfur in the silane can be varied within the range of from above 0 to about 100:1 or more, preferably from 2:1 to 20:1, more narrowly from 5:1 to 10:1. The required amount of silane will decrease as its relative sulfur content increases.

Exemplary of suitable rubber compositions are sulfur-vulcanizable synthetic rubber compositions. Representative examples of suitable rubber polymers include solution styrene-butadiene rubber (SSBR), styrene-butadiene rubber (SBR), natural rubber (NR), polybutadiene (BR), ethylene-propylene co- and ter-polymers (EP, EPDM), and acrylonitrile-butadiene rubber (NBR). The rubber composition preferably is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber. Such diene based elastomer, or rubber, may be selected, for example, from at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4- polyisoprene rubber, isoprene/butadiene rubber, styrene/isoprene/butadiene terpolymer rubber, cis-1,4-polybutadiene, medium vinyl polybutadiene rubber (35–50 percent vinyl), high vinyl polybutadiene rubber (50–75 percent vinyl), styrene/isoprene copolymers, emulsion polymerization prepared styreneibutadiene/acrylonitrile terpolymer rubber and butadiene/acrylonitrile copolymer rubber. An emulsion polymerization derived styrene/butadiene (E-SBR) might be used having a relatively conventional styrene content of 20 to 28 percent bound styrene or, for some applications, an E-SBR having a medium to relatively high bound styrene content, namely, a bound styrene content of 30 to 45 percent. Emulsion polymerization prepared styrene/butadiene/acrylonitrile terpolymer rubbers containing 2 to 40 weight percent bound acrylonitrile in the terpolymer are also contemplated as diene based rubbers for use in this invention.

See, any of U.S. Pat. Nos. 3,451,458, 5,110,969, 5,227,425 and 5,753,732, for examples of rubber compounds that can be improved with the invention with silica as a reinforcing agent. Rubber compositions based on solution polymerized styrene butadiene are preferred.

The rubber compositions, in addition to at least one elastomer of synthetic or natural origin, will contain a mineral filler, especially silica, in amounts effective for reinforcing the rubber in its vulcanized state. The silica can be of the types known, for example described in U.S. Pat. No. 4,704,414, U.S. Pat. No. 5,227,425 and U.S. Pat. No. 5,753,732, and will be employed in amounts suitable for the reinforcing tires, especially those having low rolling resistance. The silica will be employed at a level of from about 5 to about 100 parts per hundred parts of rubber, preferably at least 30 parts silica. Higher or lesser amounts can be employed where appropriate.

Precipitated silicas are preferred fillers. The silica may be characterized by having a BET surface area, as measured using nitrogen gas, preferably in the range of 40 to 600, and more usually in a range of 50 to 300 $m^2/g$. Further, the silica, as well as the aforesaid alumina and aluminosilicate, may be expected to have a CTAB surface area in a range of 100 to 220. The average mercury porosity specific surface area for the silica should be in a range of 100 to 300 $m^2/g$.

The rubber composition may be compounded by methods known in the rubber compounding art, such as mixing the various sulfur-vulcanizable constituent rubbers with various commonly used additive materials such as, for example, curing aids, such as sulfur, activators, retarders and accelerators, processing additives, such as oils, resins including tackifying resins, silicas, plasticizers, fillers, pigments, fatty acid, zinc oxide, waxes, antioxidants and antiozonants, peptizing agents, and reinforcing materials such as, for example, carbon black. Depending on the intended use of the sulfur vulcanizable and sulfur vulcanized material (rubbers), the additives mentioned above are selected and commonly used in conventional amounts.

A rubber composition may prepared by a process such as by:

(A) thermomechanically mixing, in at least one preparatory mixing step, to a temperature of 140° C. to 200° C., alternatively to 140° C. to 190° C., for a total mixing time of 1 to 20, alternatively 14 to 15, minutes for such mixing step(s)

(i) 100 parts by weight of at least one sulfur vulcanizable rubber selected from conjugated diene homopolymers and copolymers, and copolymers of at least one conjugated diene and aromatic vinyl compound, (ii) 5 to 100, preferably 25 to 80, phr (parts per hundred rubber) of particulate filler, wherein preferably the filler contains 1 to 85 weight percent carbon black (iii) 0.05 to 20 parts by weight filler of at least one sulfur-containing silane;

(B) subsequently blending therewith, in a final thermomechanical mixing step at a temperature to 50° C. to 130° C. for a time sufficient to blend the rubber, preferably between 1 to 30 minutes, more preferably 1 to 3 minutes, a curing agent at 0 to 5 phr; and optionally (C) curing said mixture at a temperature of 130 to 200° C. for about 5 to 60 minutes. An exemplary process for using silane coupling agents to manufacture silica containing tires is disclosed in PCT/US98/17391, which is incorporated herein by reference.

The rubber compositions of the invention may be employed, for example, to form shoe soles or tire parts, such as treads and sidewalls in the normal fashion as conventional silica-reinforced, sulfur vulcanizable rubber compositions.

Whereas the exact scope of this invention is set forth in the appended claims, the following specific examples illustrate certain aspects of the present invention and, more particularly, point out various aspects of the method for evaluating same. However, the examples are set forth for illustrative purposes only and are not to be construed as limitations on the present invention. The abbreviations g, mL, mm, m, psi, ppm, GC, MS, and NMR respectively represent gram, milliliter, millimeter, molar equivalent, pounds per square inch, parts per million, gas chromatography, mass spectrometry, and nuclear magnetic resonance spectroscopy; temperature is reported in degrees Centigrade. Unless stated otherwise, all reactions were run in standard laboratory glassware of various sizes at atmospheric pressure under an inert atmosphere of nitrogen, and all parts and percentages are by weight.

All references cited herein are incorporated herein as they are relevant to the present invention.

EXAMPLES

The invention may be better understood by reference to the following examples in which the parts and percentages are by weight unless otherwise indicated.

Example 1

Preparation of a 3-Triethoxysilyl-1-propyl Oligosulfide Mixture with an Average Sulfur Rank of 3.0

The reactor consisted of a 5-liter flask fitted for reflux. Heat was supplied to the flask. The system was maintained under an atmosphere of nitrogen. Bulk solids were removed from the reaction products by decantation. Solids were removed more completely by pressure filtration. Pressure filtration was accomplished in a closed polytetrafluoroethylene-coated stainless steel vessel fitted with an filter pad. Solvent was removed from the product by distillation at reduced pressure using a rotary evaporator.

A 3-triethoxysilyl-1-propyl oligosulfide mixture containing sulfur ranks 2, 3, 4, 5, 6, and 7 was prepared from 3-chloro-1-propyltriethoxysilane, anhydrous sodium sulfide, and sulfur in ethanol following methods well known in the art. This yielded a product whose distribution of sulfur ranks were determined by SFC (supercritical fluid chromatography) analysis using a carbon dioxide mobile phase. The sulfur rank distribution was found to be 21.3% disulfide, 30.5% trisulfide, 24.7% tetrasulfide, 15.1% pentasulfide, 6.4% hexasulfide, and 2.0% heptasulfide. This material was used as the starting silane to be partially desulfurized. 3-mercapto-1-propyltriethoxysilane (95.3 grams, 0.40 moles) was added to the reactor and placed under an atmosphere of nitrogen. Sodium ethoxide (27.2 grams, 0.40 moles) as a 21 weight % solution (129.5 grams) in denatured, anhydrous ethanol was added to the mercaptosilane and stirred to produce a homogeneous mixture. The aforementioned starting silane (819.2 grams) was added to the reactor. The mixture was heated with stirring to 90 deg.C. and kept at this temperature, under nitrogen for several hours. The ethanol solvent was distilled away, whereupon a yellow to brown precipitate of sodium polysulfides formed. Filtration yielded a product whose sulfur ranks were distributed as follows as determined by the aforementioned SFC procedure: 49% disulfide, 34% trisulfide, 13% tetrasulfide, 3% pentasulfide, and 1% hexasulfide.

Example 2

Preparation of High-Purity 3-Triethoxysilyl-1-propyl Disulfide

This and the following two examples demonstrate how a disulfide silane can be produced whereby thioether is suppressed by initially preparing an oligosulfide silane mixture rich in sulfur and thereby containing S3, S4 (i.e. trisulfide, tetrasulfide),and optionally higher sulfur ranks, and then desulfurizing the higher sulfur ranks by the method of the present invention, to convert the higher ranks back down to S2. The initial use of excess sulfur suppresses thioether formation which, once formed, cannot be readily converted to any other sulfur rank. The higher sulfur ranks, in contrast, can readily be converted to S2 by the method of the present invention.

The reactor system was the same as above. A 3-triethoxysilyl-1-propyl oligosulfide mixture containing sulfur ranks 2, 3, 4, and 5 was prepared from 3-chloro-1-propyltriethoxysilane, anhydrous sodium sulfide, and sulfur in ethanol following methods well known in the art. The sulfur rank distribution was found by SFC to be 63.9% disulfide, 25.8% trisulfide, 8.2% tetrasulfide, and 2.1% pentasulfide. This material was used as the starting silane to be desulfurized in the next step of the process. 3-mercapto-1-propyltriethoxysilane (243.5 grams, 1.02 moles) was added to the reactor and placed under an atmosphere of nitrogen. Sodium ethoxide (71.13 grams, 1.05 moles) as a 21 weight % solution (338.7 grams) in denatured, anhydrous ethanol was added to the mercaptosilane and stirred to produce a homogeneous mixture. The aforementioned starting silane (1569.02 grams) was added to the reactor. The mixture was stirred under nitrogen for two hours. The ethanol solvent was distilled away, whereupon a yellow to brown precipitate of sodium polysulfides formed. Filtration yielded a product whose sulfur ranks were distributed as follows as determined by gas chromatography: 0.6% monosulfide (thioether), 99.3% disulfide, and 0.1% trisulfide.

Example 3

Preparation of a 3-Triethoxysilyl-1-propyl Oligosulfide Mixture with Low Polysulfidic Sulfur Content This and the following two examples demonstrate how the complete or partial desulfurization of an oligosulfide silane composition can be coupled with an alkoxy group exchange on silicon. Ethoxy silane esters contaminated with methoxy esters were transesterified with ethanol to convert all of the methoxy esters to ethoxy esters during the desulfurization process as described in the examples.

The reactor consisted of a 5-liter flask fitted to a 25-plate Oldershaw distilling column (28 mm ID). The top of the column was fitted to a distillation head capable of delivering a variable and controllable reflux ratio. Heat was supplied to the flask. The system was maintained under an atmosphere of nitrogen. Bulk solids were removed from the reaction products by decantation. Solids were removed more completely by gravity filtration through a sintered glass frit in a vessel. Solvent was removed from the product by distillation at reduced pressure using a rotary evaporator.

A 3-triethoxysilyl-1-propyl oligosulfide mixture containing sulfur ranks 2, 3, 4, 5, and 6 was prepared (step 1) from 3-chloro-1-propyltriethoxysilane, anhydrous sodium sulfide, and sulfur in ethanol following methods well known in the art. The 3-chloro-1-propyltriethoxysilane used was contaminated with a few thousand ppm of 3-chloro-1-propylmethoxydiethoxysilane, as determined by GC and GCMS. The anticipated presence of pentaethoxymonomethoxy analogs of the hexaethoxyoligosulfide silanes was confirmed by procedures similar to those used to establish the presence of methoxy contamination in the starting 3-chloro-1-propyltriethoxysilane. The sulfur rank distribution (hexaethoxy species) was found by SFC to be 6.0 monosulfide (thioether), 73.6% disulfide, 17.5% trisulfide, 2.5 % tetrasulfide, 0.3% pentasulfide, and 0.1% hexasulfide. This material was used as the starting silane to be partially desulfurized in the next step (step 2) of the process. 3-Mercapto-1-propyltriethoxysilane (159.5 mL., 171 grams, 0.717 moles) was added to the reactor and placed under an atmosphere of nitrogen. The starting 3-mercapto-1-propyltriethoxysilane also contained methoxy contamination as the methoxy diethoxy ester, similar to that of the 3-chloro-1-propyltriethoxysilane originally used to prepare the oligosulfide mixture in step 1, but additionally containing measurable amounts of the ethoxydimethoxy ester. The total molar methoxy to ethoxy ratio of the starting 3-mercapto-1-propyltriethoxysilane used was close to 1/20. Sodium ethoxide (58.1 grams, 0.853 moles) as a 21 weight % solution (240 mL., 276 grams) in denatured, anhydrous ethanol was added to the mercaptosilane and stirred to produce a homogeneous mixture. The aforementioned starting silane (3700 grams) was added to the reactor. An additional portion of 400 mL. of ethanol was added. The mixture was stirred under an atmosphere of nitrogen and distilled with only a very slow collection of alcoholic distillate. Ethanol was added in several hundred mL. portions as needed to keep the boiling point of the mixture below 130 deg.C. for the next 4–5 days. The reflux ratio was greater than 10. The appearance of a brown precipitate was evident during this procedure, especially when the ethanol content in the flask was low. At the end of this period, the remaining ethanol solvent was rapidly distilled away with the aid of a vacuum, whereupon the formation of the brown precipitate of sodium polysulfides was completed. The remaining product was cooled and decanted to remove most of the solids. Gravity filtration yielded a product whose sulfur ranks were distributed as follows as determined by GC: 6.1% monosulfide (thioether), 93.7% disulfide, and 0.2% trisulfide.

Example 4

Variation of the Preparation of a 3-Triethoxysilyl-1-propyl Oligosulfide Mixture with Low Polysulfidic Sulfur Content The reactor was set up as in Example 3. A 3-triethoxysilyl-1-propyl oligosulfide mixture containing sulfur ranks 2, 3, 4, 5, and 6 was prepared from 3-chloro-1-propyltriethoxysilane, anhydrous sodium sulfide, and sulfur in ethanol following methods well known in the art. The 3-chloro-1-propyltriethoxysilane used was contaminated with a few thousand ppm of 3-chloro-1-propylmethoxydiethoxysilane, as determined by GC and GC/MS. The anticipated presence of pentaethoxy-monomethoxy analogs of the hexaethoxyoligosulfide silanes was confirmed by procedures similar to those used to establish the presence of methoxy contamination in the starting 3-chloro-1-propyltriethoxysilane. The sulfur rank distribution (hexaethoxy species) was found by SFC to be 6.0 monosulfide (thioether), 73.6% disulfide, 17.5% trisulfide, 2.5% tetrasulfide, 0.3% pentasulfide, and 0.1% hexasulfide. This material was used as the starting silane to be partially desulfurized in the next step of the process. 3-mercapto-1-propyltriethoxysilane (146 mL., 157 grams, 0.657 moles) was added to the reactor and placed under an atmosphere of nitrogen. The starting 3-mercapto-1-propyltriethoxysilane also contained methoxy contamination as the methoxydiethoxy ester, similar to that of the 3-chloro-1-propyltriethoxysilane originally used to prepare the oligosulfide mixture in the first step, but additionally containing measurable amounts of the ethoxydimethoxy ester. The total molar methoxy to ethoxy ratio of the starting 3-mercapto-1-propyltriethoxysilane used was close to 1/20. Sodium ethoxide (43.1 grams, 0.632 moles) as a 21 weight % solution (178 mL., 205 grams) in denatured, anhydrous ethanol was added to the mercaptosilane and stirred to produce a homogeneous mixture. The aforementioned starting silane (3673 grams) was added to the reactor. An additional portion of 400 mL. of ethanol was added. The mixture was stirred under an atmosphere of nitrogen and distilled with only a very slow collection of alcoholic distillate. Ethanol was added in several hundred mL. portions as needed to keep the boiling point of the mixture below 130 deg.C. for the next 4–5 days The reflux ratio was well in excess of 10. The appearance of a brown precipitate was evident during this procedure, especially when the ethanol content in the flask was low. At the end of this period, the remaining ethanol solvent was then rapidly distilled away with the aid of a vacuum, whereupon the formation of the brown precipitate of sodium polysulfides was completed. The remaining product was cooled and decanted to remove most of the solids. Gravity filtration then yielded a product whose sulfur ranks were distributed as follows as determined by gas chromatography: 6.3% monosulfide (thioether), 93.4% disulfide, and 0.3% trisulfide.

Example 5

Preparation of a 3-Triethoxysilyl-1-propyl Di- and Tri-Sulfide Mixture with Low Thioether and Low Higher Sulfur Rank Content The reactor was as in Example 3. A 3-triethoxysilyl-1-propyl oligosulfide mixture containing sulfur ranks 2, 3, 4, 5, and 6 was prepared from 3-chloro-1-propyltriethoxysilane, anhydrous sodium sulfide, and sulfur in ethanol following methods well known in the art. The 3-chloro-1-propyltriethoxysilane used was contaminated with a few thousand ppm of 3-chloro-1-propylmethoxydiethoxysilane, as determined by GC and GCMS. The anticipated presence of pentaethoxy-monomethoxy analogs of the hexaethoxyoligosulfide silanes was confirmed by procedures similar to those used to establish the presence of methoxy contamination in the starting 3-chloro-1-propyltriethoxysilane. The sulfur rank distribution (hexaethoxy species) was found by SFC to be 6.0 monosulfide (thioether), 73.6% disulfide, 17.5% trisulfide, 2.5% tetrasulfide, 0.3% pentasulfide, and 0.1% hexasulfide. This material was used as the starting silane to be partially desulfurized in the next step of the process. 3-mercapto-1-propyltriethoxysilane (128 mL., 137 grams, 0.576 moles) was added to the reactor and placed under an atmosphere of nitrogen. The starting 3-mercapto-1-propyltriethoxysilane also contained methoxy contamination as the methoxydiethoxy ester, similar to that of the 3-chloro-1-propyltriethoxysilane originally used to prepare the oligosulfide mixture in the first step, but additionally containing measurable amounts of the ethoxydimethoxy ester. The total molar methoxy to ethoxy ratio of the starting 3-mercapto-1-propyltriethoxysilane used was close to 1/20. Sodium ethoxide (45.4 grams, 0.667 moles) as a 21 weight % solution (187.5 mL., 216 grams) in denatured, anhydrous ethanol was added to the mercaptosilane and stirred to produce a homogeneous mixture. The aforementioned starting silane (3700 grams) was then added to the reactor. An additional 400 mL. portion of ethanol was added. The mixture was stirred under an atmosphere of nitrogen and distilled with only a very slow collection of alcoholic distillate. Ethanol was added in several hundred mL. portions as needed to keep the boiling point of the mixture below 130 deg.C. for the next 6 days The reflux ratio was well in excess of 10. The appearance of a brown precipitate was evident during this procedure, especially when the ethanol content in the flask was low. At the end of this period, the remaining ethanol solvent was rapidly distilled away with the aid of a vacuum, whereupon the formation of the brown precipitate of sodium polysulfides was completed. The remaining product was cooled and decanted to remove most of the solids. Gravity filtration then yielded a product whose sulfur ranks were distributed as follows as determined by gas chromatography: 5.8% monosulfide (thioether), 82.6% disulfide, and 11.6% trisulfide.

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is defined by the following claims. The claims are meant to cover the indicated elements and steps in any arrangement or sequence which is effective to meet the objectives intended for the invention, unless the context specifically indicates the contrary.

What is claimed is:

1. A method comprising: reacting an oligosulfidic silane containing at least one polysulfidic sulfur atom with a mercaptosilane salt.

2. A method according to claim 1 wherein the oligosulfidic silane is represented by the formula $$X^1X^2X^3SiG\text{-}S_n\text{-}GSiX^1X^2X^3$$

wherein each occurrence of G is independently a divalent group derived by substitution of alkyl, alkenyl, aryl or aralkyl wherein G can contain from 1 to 18 carbon atoms; each occurrence of $X^1$, $X^2$, and $X^3$ is independently a group selected from the group consisting of RO— and R—, wherein each occurrence of R is independently alkyl, alkenyl, aryl or aralkyl wherein R contains from 1 to 18 carbon atoms; and at least one of $X^1$, $X^2$, and $X^3$ is not R, and each occurrence of n is an integer from 3 to 20.

3. A method according to claim 2 wherein the mercaptosilane salt is represented by the formula $X^1X^2X^3SiG^1\text{-}S^-Z^+$ wherein, $X^1$, $X^2$, $X^3$, and G have the same meaning as described in claim 2 and $Z^+$ is selected from the group consisting of Group 1–3 metal cations, alkyl ammonium or ammonium.

4. A method according to claim 2 wherein $X^1$, $X^2$, and $X^3$ are selected from the group consisting of ethoxy, methoxy, and alkyl; and G is a member selected from the group consisting of $—CH_2—$, $—CH_2CH_2—$, $—CH_2CH_2CH_2—$, and $—CH_2(CH_2)_mCH_2—$, where m is an integer between 2 and 16.

5. A method according to claim 4 wherein $X^1$, $X^2$, and $X^3$ are selected from the group consisting of ethoxy, methoxy, and methyl.

6. A method according to claim 4 wherein G is $—CH_2CH_2CH_2—$.

7. A method according to claim 6 wherein the oligosulfidic silane comprises bis-(3-triethoxysilyl-1-propyl) oligosulfide compounds with a portion of the oligosulfide composed of species in which n>2.

8. A method according to claim 4 wherein $Z^+$ is $Na^+$.

9. A method according to claim 1 wherein the mercaptosilane salt is formed in situ from a mercaptosilane and a base.

10. A method according to claim 9 wherein the base is an alkoxide, hydride, or amide, of an alkali metal compounds.

11. A method according to claim 9 wherein the base is sodium alkoxide.

12. A method according to claim 9 wherein the base is sodium metal.

13. A process according to claim 1 additionally comprising the step of preparing a blend comprising rubber, silica and the product of the first step.

14. A composition comprising a mercaptosilane salt of the formula $X^1X^2X^3SiG\text{-}S^-Z^+$ wherein G is independently a divalent group derived by substitution of alkyl, alkenyl, aryl or aralkyl wherein G can contain from 1 to 18 carbon atoms; each occurrence of $X^1$, $X^2$, and $X^3$ is independently a group selected from the group consisting of RO— and R—, wherein each occurrence of R is independently alkyl, alkenyl, aryl or aralkyl wherein R contains from 1 to 18 carbon atoms; and at least one $X^1$, $X^2$, and $X^3$ is not R and $Z^+$ is a cation.

15. A composition according to claim 14 which is essentially free of other mercaptosilanes.

16. A composition comprising a salt of a mercaptosilane and an oligosulfidic silane containing at least one polysulfidic sulfur atom, wherein said oligosulfidic silane is free of direct sulfur-to-silicon bonds.

17. A composition according to claim 16 wherein the oligosulfidic silane is represented by the formula $X^1X^2X^3SiG\text{-}S_n\text{-}GSiX^1X^2X^3$ wherein each occurrence of G is independently a monovalent or polyvalent group derived by substitution of alkyl, alkenyl, aryl or aralkyl wherein G can contain from 1 to 18 carbon atoms; each occurrence of $X^1$, $X^2$, and $X^3$ is independently the group consisting of RO— and R—, wherein each occurrence of R is independently alkyl, alkenyl, aryl or aralkyl wherein R contains from 1 to 18 carbon atoms; and at least one $X^1$, $X^2$, and $X^3$ is not R, and each occurrence of n is an integer from 3 to 20.

18. A composition according to claim 17 wherein $X^1$, $X^2$, and $X^3$ are selected from the group consisting of ethoxy, methoxy, and alkyl; and G is a member selected from the group consisting of $—CH_2—$, $—CH_2CH_2—$, $—CH_2CH_2CH_2—$, and $—CH_2(CH_2)_mCH_2—$, where m is an integer between 2 and 16.

19. A composition according to claim 14 additionally comprising an alcohol solvent.

20. A composition according to claim 16 additionally comprising an alcohol solvent.

* * * * *